Figure 1:
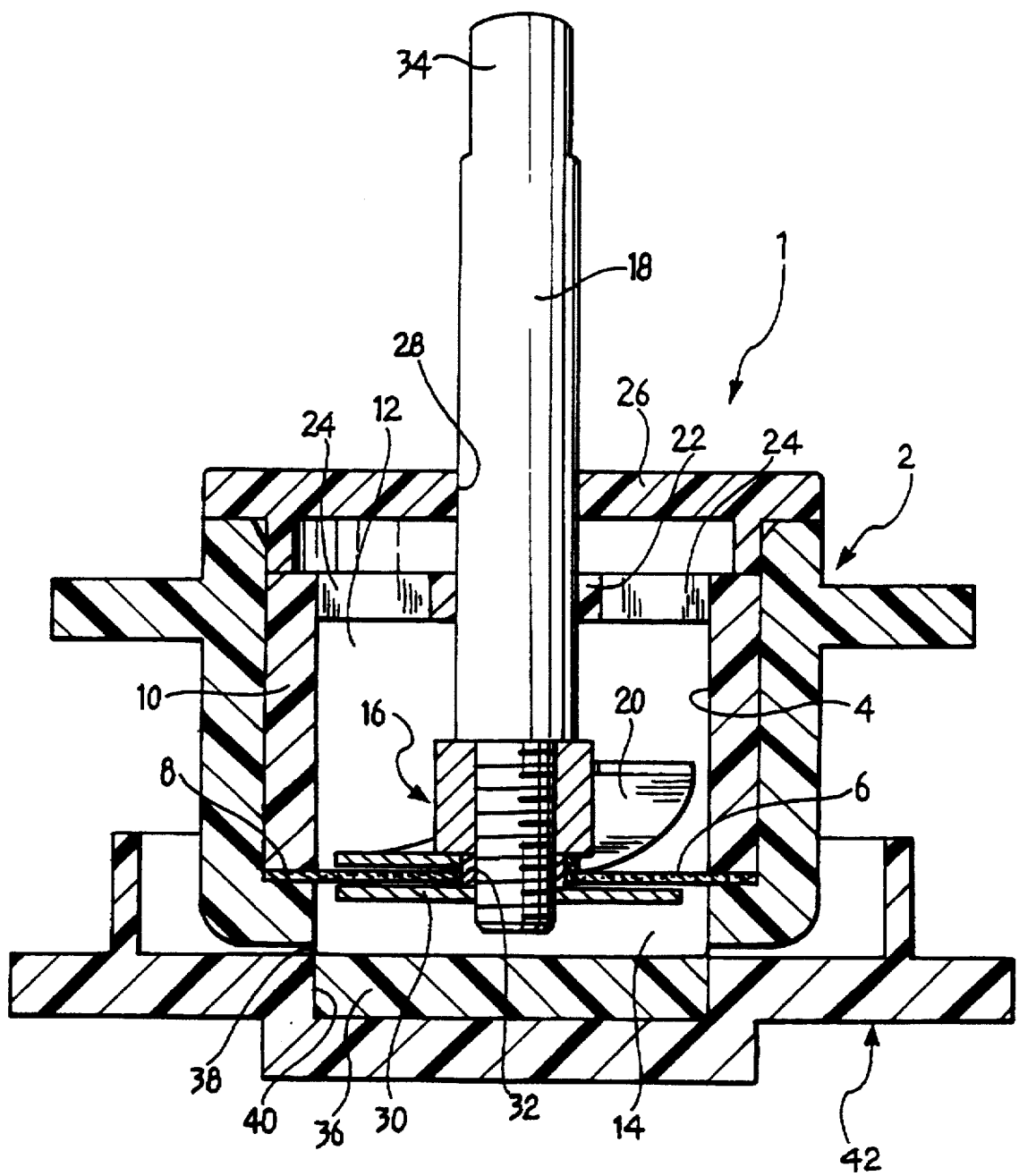

United States Patent [19] — Roggero
[11] Patent Number: 5,731,199
[45] Date of Patent: Mar. 24, 1998

[54] MECHANICAL TRITURATOR FOR BIOLOGICAL MATERIAL

[76] Inventor: Gianmarco Roggero, Via Alfieri 14, I-10090 Bruino (Torino), Italy

[21] Appl. No.: 615,282
[22] PCT Filed: Sep. 26, 1994
[86] PCT No.: PCT/EP94/03202
 § 371 Date: Mar. 27, 1996
 § 102(e) Date: Mar. 27, 1996
[87] PCT Pub. No.: WO95/09051
 PCT Pub. Date: Apr. 6, 1995

[30] Foreign Application Priority Data

Sep. 28, 1993 [IT] Italy ................. TO93A0706

[51] Int. Cl.$^6$ ................................................. C12M 3/00
[52] U.S. Cl. ............... 435/306.1; 241/82.5; 241/83; 241/88; 241/89.4; 241/194
[58] Field of Search .................. 435/306.4, 306.1; 241/83, 84, 82.5, 86, 86.1, 88.1, 89.4, 194

[56] References Cited

U.S. PATENT DOCUMENTS 1,480,969   1/1924  Thomson .
2,801,665   8/1957  Hortnagl .
3,666,187   5/1972  Norris ........................... 241/90
5,330,916   7/1994  Williams et al. ................. 435/311

FOREIGN PATENT DOCUMENTS 0 191 010 A   8/1986   European Pat. Off. ........ B02C 18/36
1309224      10/1962   France ......................... B02C 18/30
26 01 953    2/1977    Germany ....................... B02C 18/36

*Primary Examiner*—David A. Redding
*Attorney, Agent, or Firm*—Venable, Baetjer, Howard & Civiletti, LLP

[57] ABSTRACT

A mechanical triturator for biological material comprises a cylindrical housing defining a chamber in which a cutting member constituted by a perforated plate is disposed. A rotor member, mounted for rotation in the chamber, has a screw which cooperates with the cutting member in order, as a result of its rotation, to supply the biological material into contact with the cutting member and to cause the trituration thereof.

20 Claims, 3 Drawing Sheets

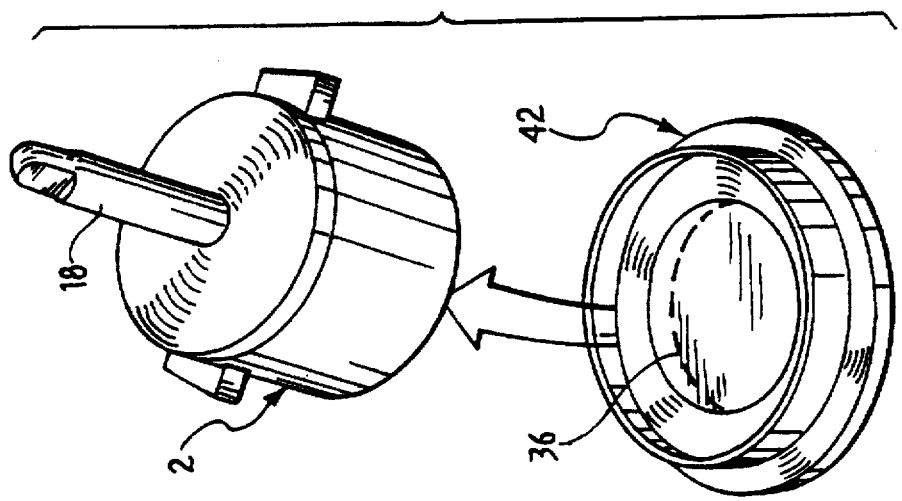
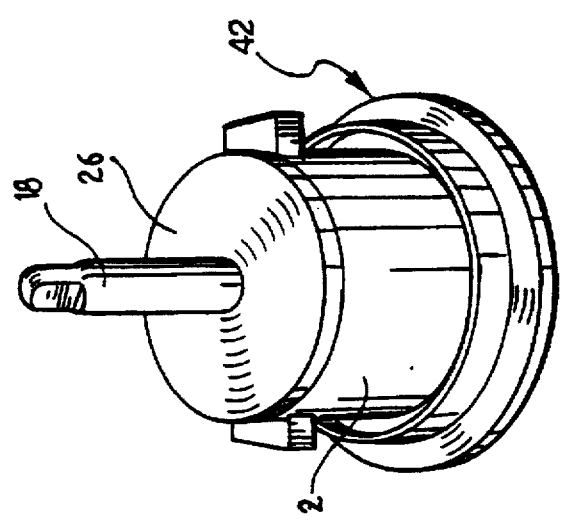
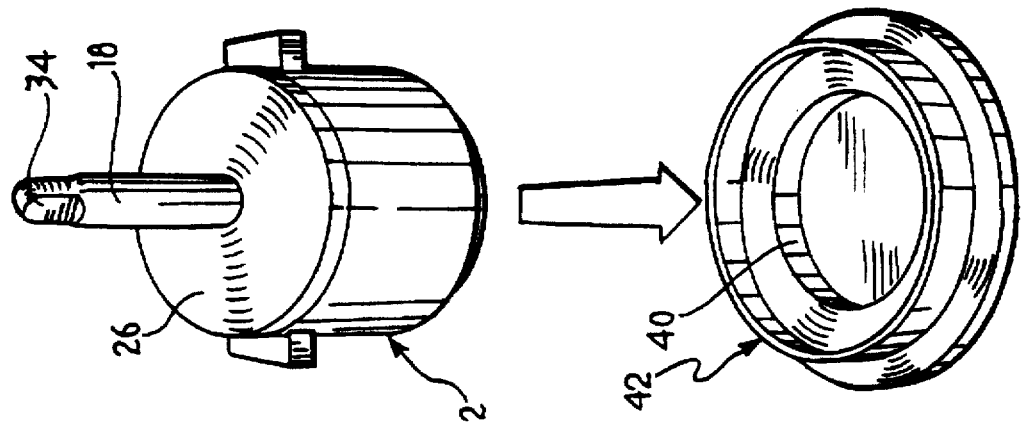

MECHANICAL TRITURATOR FOR BIOLOGICAL MATERIAL

The present invention relates to a mechanical triturator or grinder for biological materials such as animal or vegetable tissues and the like, which is suitable for laboratory and/or industrial use to produce separate cells or cell nuclei, for example, for biopsy or DNA analysis.

The object of the present invention is to provide a mechanical device which avoids lengthy and tedious mechanical chopping operations carried out with scalpels or the like and enzymatic cell-separation treatments.

According to the present invention, this object is achieved by a mechanical triturator comprising:

- a cylindrical housing 2 defining a chamber 4,
- a cutting member in the form of a foraminous plate 6 which is disposed transversely in the chamber 4 so as to define an input portion 12 for the supply of the material to be triturated and a portion 14 for collecting the triturated material, and which has a plurality of blades extending from the general plane of the plate 6 into the input portion 12,
- a rotor member 16 mounted for rotation in the chamber 4 and having a grinding member 20 which is fixed to the rotor 16 and is disposed in the input portion 12, and cooperates with the cutting member 6 in order, as a result of its rotation, to supply the biological material into contact with the blades and to cause the trituration thereof.

Figure 2:
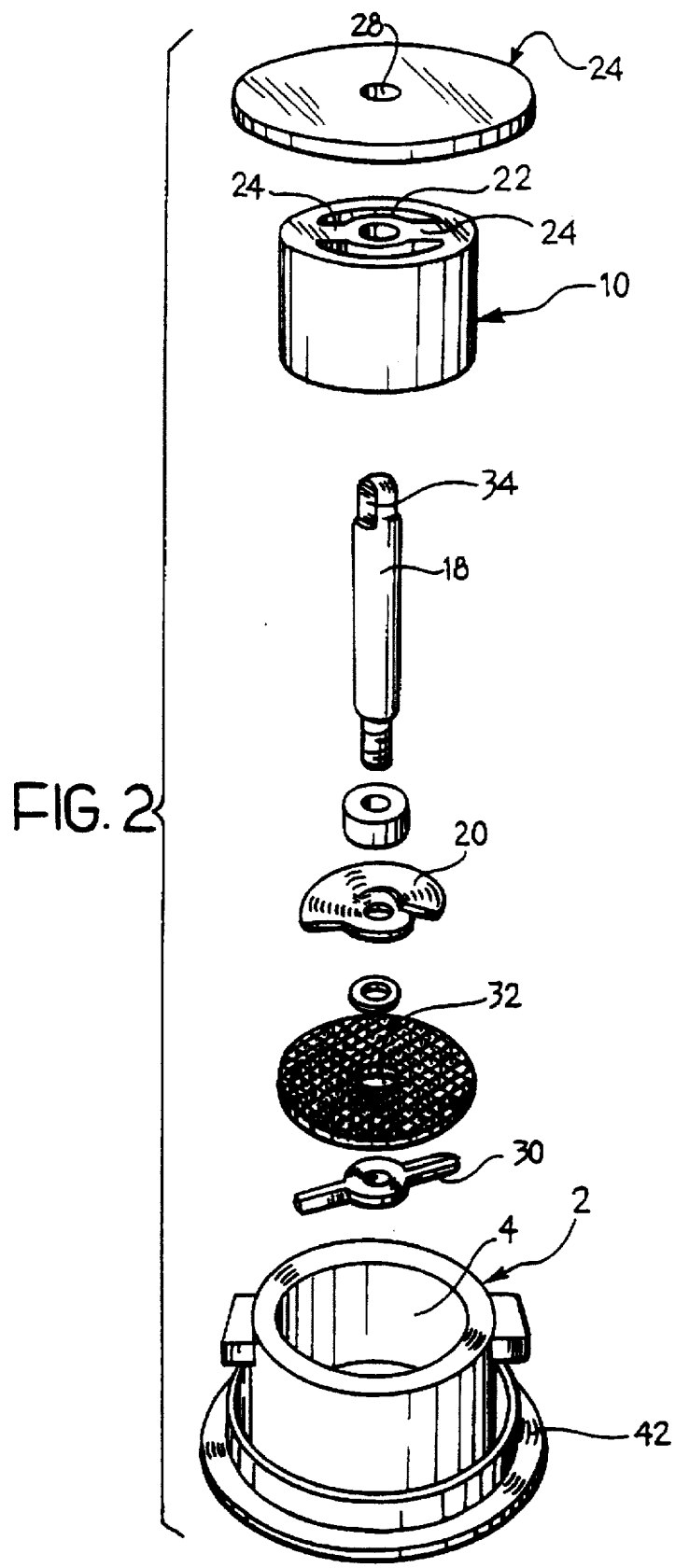

Further characteristics and advantages of the present invention will become clear in the course of the detailed description which follows, given purely by way of non-limiting example, with reference to the appended drawings, in which:

FIG. 1 is a schematic, axial section of a triturator according to the invention, FIG. 2 is an exploded perspective view of the triturator of FIG. 1, and FIGS. 3, 4 and 5 show schematically the sequence of use of the triturator according to the invention.

With reference to FIGS. 1 and 2, a triturator, indicated 1, comprises a cylindrical housing 2 of plastics material defining a chamber 4.

A cutting member constituted by a perforated plate 6 or disc is disposed transversely in the chamber 4. The plate 6 may be produced by the punching and stretching of a stainless steel plate. The perforations in the plate have preferably dimensions of between 20 and 100 µm and the edges of each microperforation constitute trituration blades. The microperforations can be produced by punches with any profile and preferably square or hexagonal profiles so that the perforated plate 6 preferably has from four to six blades surrounding each hole.

A peripheral edge of the perforated plate bears against a shoulder 8 of the cylindrical housing 2 and the perforated plate is fixed to the latter by means of a cylindrical bush 10 coupled with the cylindrical internal wall of the housing 2.

The perforated plate 6 divides the chamber 4 of the housing 2 into an input portion 12 for the supply of the material to be triturated and a portion 14 for collecting the triturated material. The blades of the perforated plate 6 are oriented towards the input portion 12.

A rotor member 16 disposed in the chamber 4 of the housing 2 comprises a shaft 18 to which a grinding member or screw 20 is fixed; the screw 20 being disposed in the input portion 12 of the chamber 4 and cooperating with the perforated plate 6 in order, as a result of its rotation at high speed, to supply the biological material into contact with the blades of the perforated plate 6 so as to cause the trituration of the material. The shaft 18 is supported for rotation by a plain bearing 22 integral with the bush 10. The bearing 22 is connected to the side walls of the bush 10 by means of two or more spokes 24 between which holes are defined for the introduction of the material to be triturated.

The upper portion of the cylindrical housing 2 is closed by a cover 26 having a central hole 28 through which the shaft 18 extends.

The rotor member 16 also comprises a sweeping blade member or rotary screw 30 having one or more flat blades. The sweeping blade member 30 is fixed to an end of the shaft 18 which projects into the collection portion 14 through a hole 32 in the perforated plate 6. The blade member 30 is adjacent and parallel to the lower surface of the plate in the collection portion and, in operation, creates an upwards flow of liquid through the holes in the plate and thus cleans the holes. The liquid which exerts this cleaning action may be contained in the biological sample since the latter is generally constituted by a suspension of tissue or aggregated cells in a liquid.

The shaft 18 has a shank 34 at its upper end for connecting it to the shaft of a motor, for example, of the turbine type, for rotating the rotor member 16.

The base of the cylindrical housing 2 is constituted by a disc 36 which is connected to the rest of the housing by means of a weakened portion 38. The disc 36 is coupled with a seat 40 in a cup-like body 42 which is intended to collect the triturated material.

With reference to FIGS. 3, 4 and 5, the housing 2 is fixed to the cup-like body 42 by the plug-in or snap-coupling of the disc 36 with the seat 40 (see FIGS. 3 and 4). Upon completion of the trituration of the material, the triturated material is collected by the removal of the cylindrical housing 2 from the base 42. During this operation, the weakened portion 38 which connects the base disc 36 to the housing 2 is torn. This ensures that the device can be used only once, to prevent problems of contamination of the material processed.

All the components of the triturator 1 except the perforated plate 6 may be made of sterilizable plastics materials suitable for use in the medical field.

The simplicity and ease of assembly of the various components of the device enable the cost to be kept to an acceptable level for disposable devices.

I claim:

1. A mechanical triturator for biological materials adapted to prepare a sample of said biological material for biopsy or DNA analysis, characterised in that it comprises:

a cylindrical housing defining a chamber, a cutting member in the form of a foraminous plate with holes having a dimension of from 20 to 100 µm in width, which is disposed transversely in the chamber so as to define within said chamber an input portion for the supply of the material to be triturated and portion for collecting the triturated material, said cutting member having a plurality of blades surrounding each hole extending from a general plane of the plate into the input portion, a rotor member mounted for rotation in the chamber and having a grinding member which is fixed to the rotor and is disposed in the input portion, and cooperates with the cutting member in the order, as a result of its rotation, to supply the biological material into contact with the blades and to cause the trituration thereof.

2. A device according to claim 1, characterised in that the rotary member comprises a sweeping blade member which is fixed for rotation with the rotor, and is disposed adjacent and parallel to the lower surface of the plate in the collection portion, said sweeping blade member being suitable for preventing the biological material from obstructing the holes during trituration.

3. A device according to claim 1, characterised in that the plate constituting the cutting member is a micro-stretched foraminous metal plate with holes having dimensions of between 20 and 100 μm in width.

4. A device according to claim 3, characterised in that the foraminous plate constituting the cutting member has from four to six blades surrounding each hole.

5. A device according to claim 1 characterised in that the housing comprises a cylindrical body having an open end with a cover for closing the input portion and a base which can be separated from the housing by the tearing of a weakened portion, the base being connectible to a cup-like container for collecting the triturated material.

6. A method for treatment of a biological material adapted to prepare a sample for biopsy or DNA analysis, by triturating said sample with a triturator according to claim 1.

7. A device according to claim 2, characterised in that the plate constituting the cutting member is a micro-stretched foraminous metal plate with holes having dimensions of between 20 and 100 μm in width.

8. A device according to claim 7, characterised in that the foraminous plate constituting the cutting member has from four to six blades surrounding each hole.

9. A device according to claim 2, characterised in that the housing comprises a cylindrical body having an open end with a cover for closing the input portion and a base which can be separated from the housing by the tearing of a weakened portion, the base being connectible to a cup-like container for collecting the triturated material.

10. A device according to claim 3, characterised in that the housing comprises a cylindrical body having an open end with a cover for closing the input portion and a base which can be separated from the housing by the tearing of a weakened portion, the base being connectible to a cup-like container for collecting the triturated material.

11. A device according to claim 4, characterised in that the housing comprises a cylindrical body having an open end with a cover for closing the input portion and a base which can be separated from the housing by the tearing of a weakened portion, the base being connectible to a cup-like container for collecting the triturated material.

12. A device according to claim 7, characterised in that the housing comprises a cylindrical body having an open end with a cover for closing the input portion and a base which can be separated from the housing by the tearing of a weakened portion, the base being connectible to a cup-like container for collecting the triturated material.

13. A device according to claim 8, characterised in that the housing comprises a cylindrical body having an open end with a cover for closing the input portion and a base which can be separated from the housing by the tearing of a weakened portion, the base being connectible to a cup-like container for collecting the triturated material.

14. A method for treatment of a biological material adapted to prepare a sample for biopsy or DNA analysis, by triturating said sample with a triturator according to claim 2.

15. A method for treatment of a biological material adapted to prepare a sample for biopsy or DNA analysis, by triturating said sample with a triturator according to claim 3.

16. A method for treatment of a biological material adapted to prepare a sample for biopsy or DNA analysis, by triturating said sample with a triturator according to claim 4.

17. A method for treatment of a biological material adapted to prepare a sample for biopsy or DNA analysis, by triturating said sample with a triturator according to claim 5.

18. A method for treatment of a biological material adapted to prepare a sample for biopsy or DNA analysis, by triturating said sample with a triturator according to claim 7.

19. A method for treatment of a biological material adapted to prepare a sample for biopsy or DNA analysis, by triturating said sample with a triturator according to claim 8.

20. A method for treatment of a biological material adapted to prepare a sample for biopsy or DNA analysis, by triturating said sample with a triturator according to claim 13.

* * * * *